(12) United States Patent
Smits

(10) Patent No.: US 11,065,505 B2
(45) Date of Patent: *Jul. 20, 2021

(54) BICYCLE TRAINER AND METHOD OF ITS OPERATION

(71) Applicant: Tacx B.V., Wassenaar (NL)

(72) Inventor: Martin Smits, Wassenaar (NL)

(73) Assignee: Tacx B.V., Wassenaar (NL)

( * ) Notice: Subject to any disclaimer, the term of this patent is extended or adjusted under 35 U.S.C. 154(b) by 74 days.

This patent is subject to a terminal disclaimer.

(21) Appl. No.: 16/420,650

(22) Filed: May 23, 2019

(65) Prior Publication Data

US 2019/0275374 A1 Sep. 12, 2019

Related U.S. Application Data

(63) Continuation of application No. 15/418,062, filed on Jan. 27, 2017, now Pat. No. 10,315,073.

(30) Foreign Application Priority Data

Jan. 28, 2016 (NL) ...................................... 2016180

(51) Int. Cl.
*A63B 24/00* (2006.01)
*G16H 20/30* (2018.01)
(Continued)

(52) U.S. Cl.
CPC ...... *A63B 24/0087* (2013.01); *A63B 21/4034* (2015.10); *A63B 21/4035* (2015.10);
(Continued)

(58) Field of Classification Search
CPC ............ A63B 24/0087; A63B 21/4034; A63B 21/4035; A63B 22/0605; A63B 69/16;
(Continued)

(56) References Cited

U.S. PATENT DOCUMENTS 4,938,475 A 7/1990 Sargeant et al.
5,890,995 A 4/1999 Bobick et al.
(Continued)

FOREIGN PATENT DOCUMENTS

| NL | 1019154 | 4/2003 |
|---|---|---|
| NL | 2001323 | 8/2009 |
| WO | 92/16267 | 10/1992 |

OTHER PUBLICATIONS

Track Simulation, http://www.cyclus2.com/en/track-simluation.htm, published prior to Jan. 27, 2017.

*Primary Examiner* — Sundhara M Ganesan
(74) *Attorney, Agent, or Firm* — Samuel M. Korte; Max M. Ali

(57) ABSTRACT

Method for operating a bicycle trainer, and such a bicycle trainer comprising a stand with a seat, handlebars and rotatable pedals, or such a bicycle trainer comprising a stand for mounting a bicycle frame with a seat, handlebars and rotatable pedals, wherein the stand incorporates an electronically variable brake acting directly or indirectly on the rotatable pedals with a braking resistance that depends on a computer-controlled predetermined setting, wherein the predetermined setting is variable and wherein said setting depends on selected parameters to reflect a simulated surface condition of a road.

12 Claims, 2 Drawing Sheets

(51) Int. Cl.
*A63B 21/00* (2006.01)
*A63B 22/06* (2006.01)
*A63B 69/16* (2006.01)
*A63B 71/06* (2006.01)

(52) U.S. Cl.
CPC .......... *A63B 22/0605* (2013.01); *A63B 69/16* (2013.01); *A63B 71/0622* (2013.01); *G16H 20/30* (2018.01); *A63B 2024/009* (2013.01); *A63B 2069/163* (2013.01); *A63B 2069/165* (2013.01); *A63B 2071/0638* (2013.01); *A63B 2220/78* (2013.01)

(58) Field of Classification Search
CPC ........ A63B 71/0622; A63B 2071/0638; A63B 2220/78; A63B 2024/009; A63B 2069/163; A63B 2069/165; G16H 20/30
See application file for complete search history.

(56) References Cited

U.S. PATENT DOCUMENTS

| | | | | |
|---|---|---|---|---|
| 2005/0008992 | A1* | 1/2005 | Westergaard | A63B 24/00 434/61 |
| 2007/0010377 | A1* | 1/2007 | Wu | A63B 69/16 482/61 |
| 2007/0054782 | A1* | 3/2007 | Lin | A63B 21/015 482/57 |
| 2009/0270227 | A1* | 10/2009 | Ashby | G06F 19/3481 482/8 |
| 2010/0062908 | A1* | 3/2010 | Hamilton | A63B 24/0087 482/61 |
| 2010/0062909 | A1* | 3/2010 | Hamilton | A63B 21/00192 482/61 |
| 2011/0172059 | A1* | 7/2011 | Watterson | A63B 24/0062 482/5 |
| 2013/0059698 | A1* | 3/2013 | Barton | A63B 21/0051 482/63 |
| 2013/0274067 | A1* | 10/2013 | Watterson | A63B 21/0051 482/5 |
| 2014/0171266 | A1* | 6/2014 | Hawkins, III | A63B 21/00069 482/5 |
| 2014/0243156 | A1* | 8/2014 | Cohen | A63B 71/0622 482/51 |
| 2015/0011362 | A1* | 1/2015 | Oh | A63F 13/245 482/9 |
| 2015/0065309 | A1* | 3/2015 | Bauer | A63B 21/0058 482/61 |
| 2016/0236036 | A1* | 8/2016 | Kalogiros | A63B 21/0058 |

* cited by examiner

BICYCLE TRAINER AND METHOD OF ITS OPERATION

RELATED APPLICATIONS

The present application is a continuation of, and claims priority benefit to, co-pending and commonly assigned U.S. non-provisional patent application entitled, "BICYCLE TRAINER AND METHOD OF ITS OPERATION," application Ser. No. 15/418,062, filed Sep. Jan. 27, 2017, which in turn claims priority to Netherlands Patent Application No. 2016180, entitled "Bicycle Trainer and Method of its Operation", filed on Jan. 28, 2016. Each of the above identified applications are incorporated herein by specific reference.

BACKGROUND

The present invention relates to a bicycle trainer comprising a stand with a seat, handlebars and rotatable pedals, or comprising a stand for mounting a bicycle frame with a seat, handlebars and rotatable pedals, wherein the stand incorporates an electronically variable brake acting directly or indirectly on the rotatable pedals with a braking resistance that depends on a computer-controlled predetermined setting. The invention also relates to a method to operate such a bicycle trainer.

The invention reflects both a so-called home trainer which is an integrated device with a seat, handlebars and pedals, as well as a bicycle trainer frame which is equipped to receive a bicycle with or without its wheels, and wherein the bicycle has a seat, handlebars and pedals. The instant invention applies to both types of trainers.

Both NL-A-2001323 and NL-A-1019154 in the name of the applicant disclose the second type of bicycle trainer that receives a frame of a bicycle or a complete bicycle. In the known bicycle trainer, the braking resistance depends on a virtual path that the cyclist passes, so that the resistance can be said to be time dependent although it merely corresponds with variations relating to an upward or down-ward inclination of the virtual path of the cyclist.

From www.cyclus2.com/en/track-simulation.htm it is known to control several factors to improve the real-life experience of a training exercise by calculating and setting the braking resistance during an indoor training as how they appear in a real scenario, depending on: air resistance; downhill force; and rolling friction.

The calculation, which is directly bearing on the brake torque for the setting of the load for the athlete, is carried out in real time and in dependence of the cycler's velocity (to reflect air resistance), weight and material.

WO92/16267 relates to a simulation system comprising a bicycle combined with a computer and video display. The simulation system comprises a bicycle model which queries whether the bicycle is off road. In the affirmative case the modeling software applies an additional braking force for rough terrain.

SUMMARY

With the invention, it is aimed to further improve the real-life experience with the bicycle trainer and with its method of operation.

For that purpose, the method of operating the bicycle trainer as well as the bicycle trainer of the invention are embodied with the features of one or more of the appended claims.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings.

DETAILED DESCRIPTION

Figure 1:
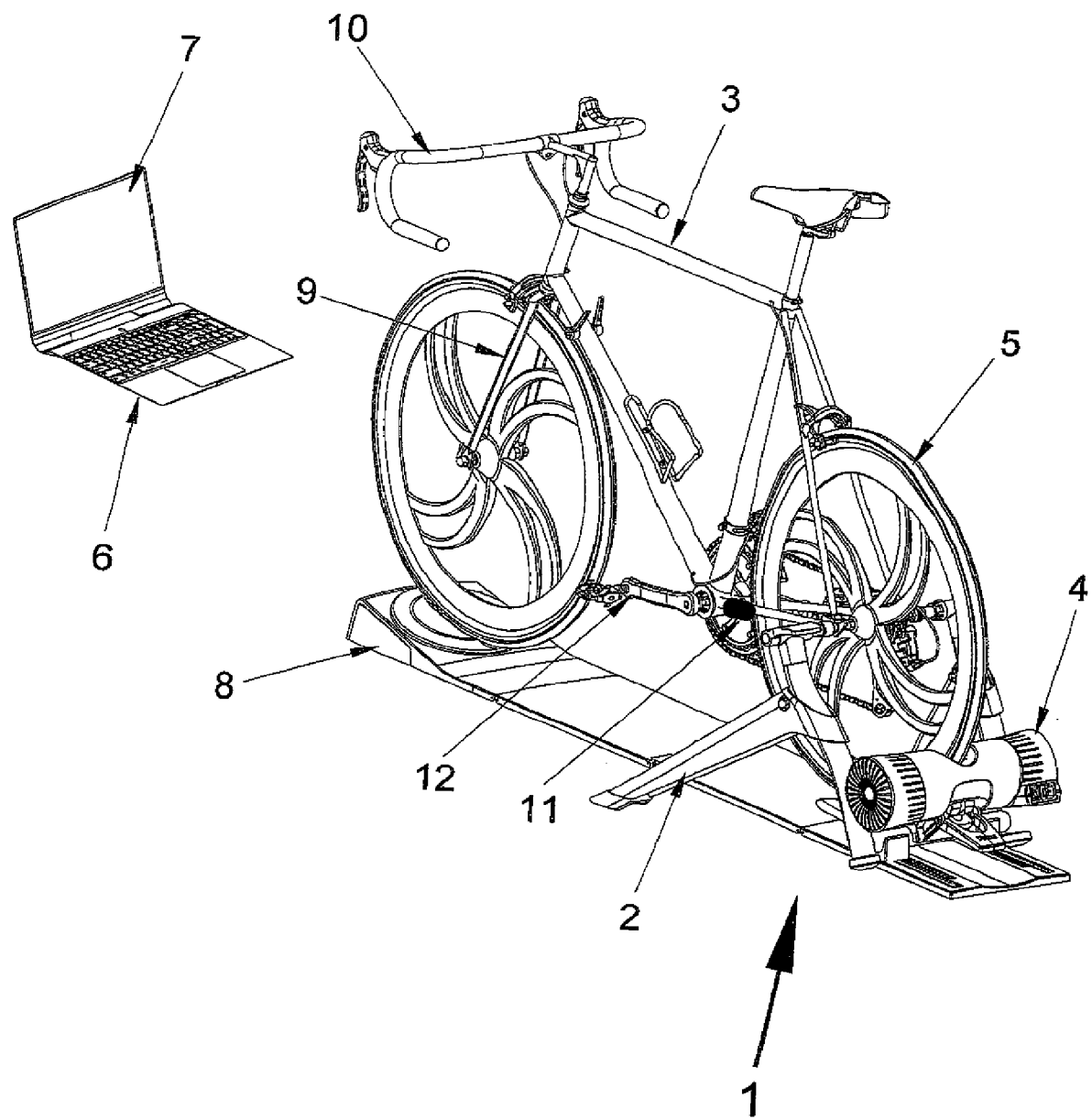
FIG. 1 shows a bicycle trainer for use according to the invention.

Generally speaking, the bicycle trainer of the invention has the feature that the predetermined setting is variable and depends on selected parameters to reflect a simulated surface condition of a road. The proposal to make the braking resistance to depend on a simulated surface condition of a virtual road is ground-breaking and an entirely novel approach for indoor bicycle training devices. Different cycle courses can thus be simulated, to note when it concerns the simulation of a brick road it is appropriate that the predetermined setting is time variable with variations predominantly of a fixed frequency. If on the other hand the simulated road involves cobblestones it is appropriate that the predetermined setting is time variable with variations containing a mixture of fixed frequencies. The various road conditions can thus generally speaking preferably be simulated by providing that the predetermined setting is time variable with variations within a predetermined frequency band.

Also, other fields of endeavor can be simulated with the bicycle trainer of the invention. Although it is known from the prior art to provide that the predetermined setting is speed dependent, wherein the speed reflects a simulated forward speed of a user that drives the pedals, the invention now provides that the said setting of the braking resistance inversely correlates with said forward speed. This is an elegant manner to simulate cycling in a sandy or muddy terrain wherein cycling gets harder with diminishing speed.

When the aim is to simulate cycling on a snowy or icy road it is best to provide that the predetermined setting is depending on a force applied to the pedals, wherein the braking resistance is inversely correlated to said force. When too much force is applied to the pedals the braking resistance suddenly drops down to a very low level which actually happens when cycling in a snowy or icy terrain.

The invention will hereinafter be further elucidated with reference to the drawing of two exemplary embodiments of the setting of a braking resistance of a bicycle trainer according to the invention that is not limiting as to the appended claims.

The applicant remarks that in principle it is unnecessary to show with reference to a drawing the construction of a bicycle trainer that according to the preamble comprises a stand with a seat, handlebars and rotatable pedals, or that comprises a stand for mounting a bicycle frame with a seat, handlebars and rotatable pedals, wherein the stand incorporates an electronically variable brake acting directly or indirectly on the rotatable pedals with a braking resistance that depends on a computer-controlled predetermined setting. These types of bicycle trainers are well known from day to day life, as well as from prior art documents such as NL-A-2001323 and NL-A-1019154. To avoid however any doubt on the sufficiency of disclosure of the instant invention reference is nevertheless made to FIG. 1 to show a bicycle trainer in accordance with NL-A-1019154, which can be arranged as discussed hereinafter with the features of the invention.

FIG. 1 shows an example of a bicycle trainer 1 of the type comprising a stand 2 which can receive a bicycle 3. The stand 2 is provided with a braking organ 4 which provides a braking resistance to a back wheel 5 of the bicycle 3. Since the bicycle's pedals 12 are connected with said back wheel 5 through a bicycle chain, the pedals 12 also experience the braking resistance as set by the braking organ 4.

The shown bicycle trainer 1 further has a computer 6 which is provided with a visual display unit 7 to show the user of the bicycle trainer 1 a simulated trajectory of a road on which the user virtually cycles. The earlier mentioned braking organ 4 thereby receives signals from the computer 6 for setting the braking resistance of the braking organ 4.

A further feature that is shown in the figure which is however not essential to the invention, is a rotational sensor 8 linked to the front wheel fork 9 of the bicycle 3. This rotational sensor 8 can be linked to the computer 6 to register steering movements with the handlebars 10 of the bicycle 1. Further the figure shows a nonessential sensor 11 which is arranged to detect each passing of a pedal 12, which can be used to measure the user's cadence during his exercise on the pedals of the bicycle.

Preferably further the braking organ 4 is built together with a sensor for measuring the rotational speed of the driven back wheel 5 of the bicycle 3, and the computer 6 is in a particular embodiment arranged to use this rotational speed of the back wheel 5 for the setting of the braking resistance as explained hereinafter.

The following discussion concentrates on the contribution that the invention provides to the prior art, which is elucidated by reference to two non-limiting examples. Both examples as reflected by FIG. 3 and FIG. 4 show that the invention provides a predetermined setting of the braking resistance which is variable and made dependent on selected parameters to reflect a simulated surface condition of a road.

Figure 2:
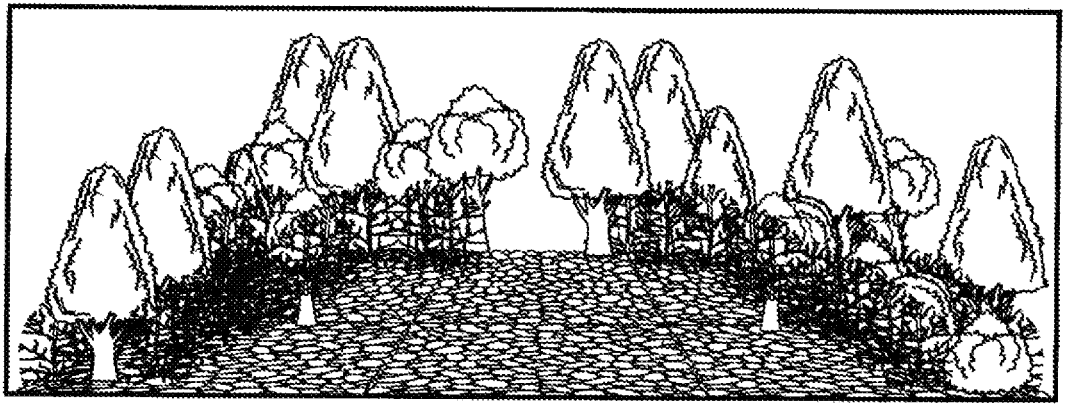
FIG. 2 shows an example of a cobblestone road.
Figure 3:
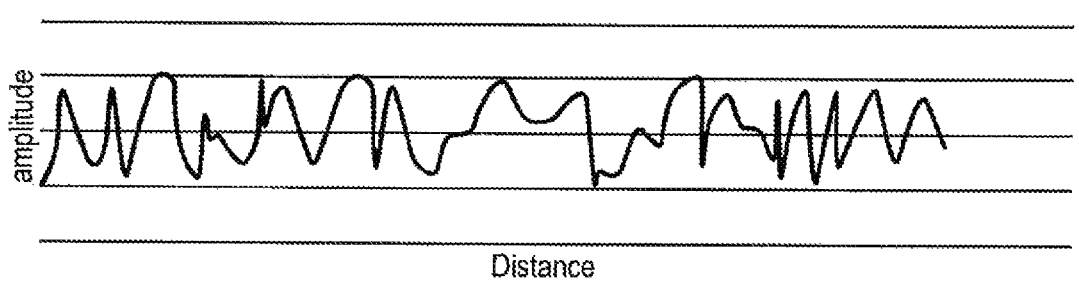
FIG. 3 shows the development over time of the setting of a braking resistance for simulating a cobblestone road as shown in FIG. 2.

In FIG. 3 it is shown that amplitude and frequency of the setting of the braking resistance is used to simulate a cobblestone road, an example of which is shown in FIG. 2. For that purpose of simulating the cobblestone road of FIG. 2, the predetermined setting of the braking resistance is shown in FIG. 3 to be time variable with variations containing a mixture of several fixed frequencies.

Figure 4:
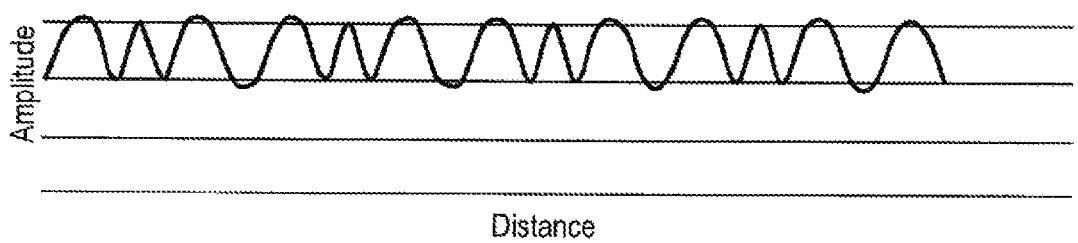
FIG. 4 shows the development over time of the setting of a braking resistance for simulating a regular brick road.

In FIG. 4 another example is shown that relates to the predetermined setting of the braking resistance as being time variable with variations predominantly of a fixed frequency, which better reflects the conditions of a normal brick road.

Numerous other variations in the predetermined setting of the braking resistance of the bicycle trainer 1 are feasible to simulate other road conditions or road materials, to note without intent to exhaust the possible variations: a setting of the braking resistance that inversely correlates with a simulated forward speed of a user of the bicycle trainer 1, so as to simulate cycling in a sandy or muddy terrain wherein cycling gets harder with lower speeds. Another option may be to simulate cycling on a snowy or icy road by providing that the predetermined setting is depending on a force applied to the pedals 12, and wherein the braking resistance is inversely correlated to said force so as to reflect that said resistance breaks down when too much force is applied to the pedals 12.

Although the invention has been discussed in the foregoing with reference to an exemplary embodiment relating to the bicycle trainer of the invention, the invention is not restricted to these particular embodiments which can be varied in many ways without departing from the invention. The discussed exemplary embodiments shall therefore not be used to construe the appended claims strictly in accordance therewith. On the contrary the embodiments are merely intended to explain the wording of the appended claims without intent to limit the claims to these exemplary embodiments. The scope of protection of the invention shall therefore be construed in accordance with the appended claims only, wherein a possible ambiguity in the wording of the claims shall be resolved using these exemplary embodiments.

What is claimed is:

1. A bicycle trainer comprising:
    a computer; and
    an electronically variable brake configured to apply a braking resistance to rotatable pedals associated with a bicycle,
    wherein the computer is coupled with the variable brake to control the braking resistance to simulate a surface condition of a road, wherein the braking resistance is controlled by utilizing a time variable setting with variations within a frequency band which depend on the simulated surface condition of the road.

2. The bicycle trainer of claim 1, wherein the time variable setting has variations predominantly of a fixed frequency.

3. The bicycle trainer of claim 1, wherein the time variable setting has variations containing a mixture of fixed frequencies.

4. The bicycle trainer of claim 1, wherein the braking resistance is further controlled based on a simulated forward speed of the bicycle.

5. The bicycle trainer of claim 1, wherein the braking resistance inversely correlates with the simulated forward speed of the bicycle.

6. The bicycle trainer of claim 1, wherein the braking resistance is further controlled based on force applied to the pedals.

7. The bicycle trainer of claim 6, wherein the braking resistance inversely correlates to the force.

8. A bicycle trainer comprising:
    a computer; and
    an electronically variable brake configured to apply a braking resistance to rotatable pedals associated with a bicycle,
    wherein the computer is coupled with the variable brake to control the braking resistance to simulate a surface condition of a road, wherein the braking resistance is controlled by utilizing a time variable setting with variations within a frequency band which depend on the simulated surface condition of the road and the braking resistance inversely correlates with a simulated forward speed of the bicycle.

9. The bicycle trainer of claim 8, wherein the time variable setting has variations predominantly of a fixed frequency.

10. The bicycle trainer of claim 8, wherein the time variable setting has variations containing a mixture of fixed frequencies.

11. The bicycle trainer of claim 8, wherein the braking resistance is further controlled based on force applied to the pedals.

12. The bicycle trainer of claim 11, wherein the braking resistance inversely correlates to the force.

\* \* \* \* \*